(12) United States Patent
Dayal

(10) Patent No.: US 8,086,469 B2
(45) Date of Patent: Dec. 27, 2011

(54) PHARMACEUTICAL CLEARINGHOUSE METHOD AND SYSTEM

(76) Inventor: Sandeep Dayal, Long Grove, IL (US)

( * ) Notice: Subject to any disclaimer, the term of this patent is extended or adjusted under 35 U.S.C. 154(b) by 795 days.

(21) Appl. No.: 11/692,639

(22) Filed: Mar. 28, 2007

(65) Prior Publication Data

US 2007/0233517 A1    Oct. 4, 2007

Related U.S. Application Data

(60) Provisional application No. 60/744,029, filed on Mar. 31, 2006.

(51) Int. Cl.
*G06F 17/60* (2006.01)
*G06Q 50/00* (2006.01)

(52) U.S. Cl. ........................................................ 705/2

(58) Field of Classification Search .................. 705/2
See application file for complete search history.

(56) References Cited

U.S. PATENT DOCUMENTS

| | | |
|---|---|---|
| 6,804,787 B2 | 10/2004 | Dick |
| 6,879,959 B1 | 4/2005 | Chapman et al. |
| 2002/0128860 A1 * | 9/2002 | Leveque et al. ............... 705/2 |
| 2003/0055727 A1 * | 3/2003 | Walker et al. ................ 705/14 |
| 2004/0236607 A1 | 11/2004 | Kost et al. |
| 2005/0015277 A1 | 1/2005 | Mau |
| 2005/0240473 A1 | 10/2005 | Ayers, Jr. et al. |

OTHER PUBLICATIONS

Harmon et al., Outpatient Medication Assistance Program in a rural setting: The Central Louisiana Medication Access Program, American Journal of Health-System Pharmacy, 2004;61(6), http://www.medscape.com/viewarticle/472700_3.*

* cited by examiner

*Primary Examiner* — Gerald J. O'Connor
*Assistant Examiner* — Hiep V Nguyen
(74) *Attorney, Agent, or Firm* — Onello & Mello, LLP; David M. Mello

(57) ABSTRACT

A pharmaceutical clearinghouse establishes relationships with a set of foundations and a set of pharmaceutical providers; in response to the clearinghouse receiving a patient request for a pharmaceutical from a foundation, the clearinghouse obtains a subsidy from at least one provider and directs the subsidy to the foundation. The subsidy can be cash, in-kind drug, or a combination thereof.

24 Claims, 6 Drawing Sheets

Pharmaceutical Drug Manufacturer Economics on PAP – Typical Biologic Drug

|  | Market Share | | Market Share Adjusted |
|---|---|---|---|
|  |  |  | 30% |
| Revenue | | | |
| Revenue at retail price of drug[1] | | $ 15,000 | $ 4,500 |
| Revenues lost to lack of full regimen compliance[2] | 20% | $ (3,000) | $ (900) |
| Net revenue | | $ 12,000 | $ 3,600 |
| Variable Costs | | | |
| Distribution costs[3] | 10.0% | $ 1,500 | $ 450 |
| Costs of Goods Sold[3] | 12.5% | $ 1,875 | $ 563 |
| Royalties[3] | 12.5% | $ 1,875 | $ 563 |
| Average co-pay subsidy at payout rate[4] | 30.0% | $ 4,095 | $ 3,276 |
| Foundation administrative costs[5] | 20.0% | $ 819 | $ 655 |
| Net variable costs | | | $ 5,506 |
| Net Contribution | | $ — | $ (1,906) |

Notes:
[1] Retail revenues assume full-year use at indicated dosage. Market share adjusted revenues are retail revenues multiplied by market share.
[2] Patients do not fully comply with the prescribed dosage levels or adjust to the time between dosages.
[3] Costs allocated in proportion to share since only in those cases does the manufacturer drug is sold.
[4] Average patient assessed to receive 80% of the maximum possible co-pay under standard Part D benefit and pays for all brands.
[5] Foundation cost of 20% of distributed funds are typical – and apply to funds from the manufacturer and competing brands.

*FIG. 1 (PRIOR ART)*

| Market Share | 10% | 20% | 30% | 40% | 50% | 60% | 70% | 80% | 90% | 100% |
|---|---|---|---|---|---|---|---|---|---|---|
| Variable Contribution | $ (2,390) | $ (2,061) | $ (1,906) | $ (1,234) | $ (396) | $ 118 | $ 734 | $ 1,480 | $ 2,144 | $ 2,810 |
| Revenue transferred to competition | $ 10,800 | $ 9,600 | $ 8,400 | $ 7,200 | $ 6,000 | $ 4,800 | $ 3,600 | $ 2,400 | $ 1,200 | $ — |

*FIG. 2*

| Clearinghouse Model Illustration - 2 Branded + 1 Low Cost | | | | | |
|---|---|---|---|---|---|
| Patients | ... On Brand X | ... On Brand Y | ... On Brand Z | Totals | Disbursements |
| Foundation A | 50 | 200 | 25 | 275 | $ 600,000 |
| Foundation B | 250 | 500 | 25 | 775 | $ 1,850,000 |
| Foundation C | 250 | 250 | 50 | 550 | $ 1,575,000 |
| Foundation D | 50 | 50 | 300 | 400 | $ 1,475,000 |
| Total | 600 | 1,000 | 400 | 2,000 | $ 5,500,000 |
| Share of patients (market share) | 30% | 50% | 20% | 100% | |
| Retail Price of Drug | $15,000 | $3,500 | $15,000 | | |
| Average Assistance provided (incl. Foundation costs) | $4,000 | $1,500 | $4,000 | | |
| Brands participating in assistance | Yes | No | Yes | | |
| Total funding needed | $2,400,000 | $1,500,000 | $1,600,000 | $5,500,000 | |
| Funding needed for to cover participant brands only | $ 2,400,000 | $ - | 1,600,000 | $4,000,000 | |
| Ratio of total vs. participant brand required assistance | | | 138% | | |
| Payments to Clearinghouse | $3,300,000 | $0 | $2,200,000 | $5,500,000 | |
| Funding applied toward contributing brand | 73% | N/A | 73% | | |
| Price after distribution margin (10%) | $ 13,500 | 3,150 | 13,500 | | |
| Effective assistance per patient | $ 5,500 | $ - | 5,500 | | |
| Effective discount on drug | 41% | 0% | 41% | | |

*FIG. 4*

| Clearinghouse Model Illustration - Low Cost Drug Preference | | | | | |
|---|---|---|---|---|---|
| Patients | ... On-Brand X | ... On Brand Y | ... On Brand Z | Totals | Disbursements |
| Foundation A | 50 | 200 | 25 | 275 | $ 600,000 |
| Foundation B | 250 | 500 | 25 | 775 | $ 1,850,000 |
| Foundation C | 250 | 250 | 50 | 550 | $ 1,575,000 |
| Foundation D | 50 | 50 | 300 | 400 | $ 1,475,000 |
| Total | 600 | 1,000 | 400 | 2,000 | $ 5,500,000 |
| Share of patients (market share) | 30% | 50% | 20% | 100% | |
| Retail Price of Drug | $15,000 | $3,500 | $15,000 | | |
| Average Assistance provided (incl. Foundation costs) | $4,000 | $1,500 | $4,000 | | |
| Brands participating in assistance | Yes | Yes | No | | |
| Total funding needed | $2,400,000 | $1,500,000 | $1,600,000 | $5,500,000 | |
| Funding needed for to cover participant brands only | $ 2,400,000 | $ 1,500,000 | - | $3,900,000 | |
| Ratio of total vs. participant brand required assistance | | | | 141% | |
| Payments to Clearinghouse | $4,000,000 | 1,500,000 | $0 | $5,500,000 | |
| Funding applied toward contributing brand | 60% | 100% | N/A | | |
| Price after distribution margin (10%) | $ 13,500 | $ 3,150 | 13,500 | | |
| Effective assistance per patient | $ 6,667 | $ 1,500 | - | | |
| Effective discount on drug | 49% | 48% | 0% | | |

FIG. 5

PHARMACEUTICAL CLEARINGHOUSE METHOD AND SYSTEM

CROSS REFERENCE TO RELATED APPLICATIONS

This application claims the benefit under 35 U.S.C. §119 (e) of U.S. Provisional Application No. 60/744,029, filed Mar. 31, 2006, entitled PHARMACEUTICAL CLEARINGHOUSE METHOD AND SYSTEM.

FIELD OF INTEREST

The present inventive concepts relate to the field of pharmaceuticals, and more specifically to systems and methods for distributing pharmaceuticals and subsidies relating to healthcare related treatment costs to qualified patients via foundations.

BACKGROUND

Two segments of patients require some form of subsidy or assistance in accessing prescription drugs or other treatments. Drug manufacturers assist indigent, uninsured patients typically by providing them with free drug. They assist low income (but not necessarily indigent), under-insured patients indirectly through drug discounts in one form or another. In the case of Medicare and Medicaid patients, anti-kick back statutes and civil monetary penalties can be implicated if these programs are not properly structured. The Office of Inspector General (OIG) is the branch of the United States government charged with oversight over such matters.

Medicare launched the Part D prescription drug plan (PDP) on Jan. 1, 2006. Up to thirty million Americans were anticipated to sign up for Part D coverage by the end of 2006, and likely more later. The Part D prescription drug plan is designed to encourage patients to seek out lower cost drugs and therapeutic alternatives. The program typically requires the patient to cover the first $250 of prescription drug costs themselves, pays 75% of the amount thereafter up to $2,250, after which there is no coverage or a "donut hole" until the patient reaches $5,100 in total drug costs, after which they pay only 5% in co-pay. In addition, the patients must pay a monthly premium of $25-40, depending on their specific plan. The plan itself is offered by participating private insurers who in turn are subsidized by Medicare. Patients must sign up for Part D coverage by May 1, 2006 or risk paying higher premium (e.g, which could escalate by 1% per month). For patients on high cost drugs, the co-pay and premium can exceed $4,000 per year, which for lower income families can represent a life-transforming burden (the average US household has about $45,000 of annual income spread across 2.6 family members). Likewise, some patients with Part B coverage also face a 20% co-pay on their treatments.

Historically, the pharmaceutical industry supported many of the Medicare underinsured with free drugs as a stop-gap measure, knowing that a prescription drug benefit was coming. Now, that the Part D program is operational, many drug manufacturers have announced their intention to end these free drug programs for Medicare patients past May when the Part D enrollment period comes to an end (although the deadline can be extended). Under the donut hole coverage structure, many patients that currently receive drug for free under such programs face out-of-pocket costs as high as $4,000 per year (e.g. for a biologic drug that costs $15,000/ year). Drug manufacturers have offered to discount these drugs, but are wary of running afoul of the anti-kickback statutes. To summarize, the relevant statutes include:

1. Civil Monetary Penalties (CMP) provision (Social Security Act §1128A (a)(5)): Civil statute prohibiting the giving of something of value to Medicare or Medicaid patients that the donor knows, or should know, is likely to influence the patient's selection of a particular provider or supplier of any item payable by Medicare or Medicaid.

2. Anti-kickback statute (Social Security Act §1128B(b)): Criminal statute prohibiting the knowing and willful offer, payment, solicitation, or receipt of any remuneration to induce or reward referrals of items or services payable by a Federal health care program. Remuneration includes transfer of anything of value, directly or indirectly, overtly or covertly, in cash or in kind. The "one purpose test" is relevant, i.e. if you do 15 things that are all good but one that violates the anti-kickback statues, then you are liable. Statute applies to parties on both sides of the transaction.

Currently, pharmaceutical drug manufacturers are allowed to assist Medicare Part D patients through cash donations to bona fide independent charities. There are five OIG mandated requirements that apply to such arrangements: (1) the manufacturer can have no influence or control over the program, (2) the assistance is awarded in a truly independent manner (i.e., no link between a manufacturer's donation and beneficiary's receipt of assistance), (3) the assistance is awarded without regard to the manufacturer's interests or beneficiary's choice of provider (i.e. which doctor or pharmacy), (4) the assistance is awarded based on reasonable, verifiable, and uniform measures of financial need, and (5) there is no data exchange that allows a manufacturer to correlate its donations to the number of prescriptions subsidized by the charity. Contributions can be limited to specific disease states, but not so narrowly that only one of many available brands qualifies. Product contributions (in lieu of cash), while eligible for TrOOP (patient's True Out Of Pocket Costs or co-pay) per CMS, are problematic since they can create a direct correlation between the donation and the use of the product, particularly if that one brand is the only option offered by the charity.

There are a number of foundations that assist under-insured patients with out-of-pocket costs. They include Patient Services Inc. (PSI), Patient Advocate Foundation, Chronic Disease Fund, National Organization for Rare Disorders, Patient Access Network Foundation (PANF) and the Healthwell Foundation.

The independent charity model offers many benefits and helps to address a number of concerns around the Civil Monetary Provisions (CMP) and the Anti-Kickback (AK) statutes. However, over the few years, a number of limitations of this model have become evident.

Drug manufacturers are reluctant to contribute funds given the strong possibility of subsidizing direct non-generic competitors: Drug manufacturers are willing to assist under-insured patients by discounting their drugs substantially in some form or fashion, while still retaining a positive contribution margin. This is different from programs directed at the uninsured, where the manufacturers give away free drug effectively at a loss up to the limits of their charitable budgets and means. Currently, a foundation must assist patients without regard to the brand of drug prescribed, including generics. This ensures that a physician's treatment choice is not biased towards brands that provide assistance, but is instead determined solely based on medical need. Also, in this way generic drugs, which provide an important policy lever for reigning in health costs, are not disadvantaged even when they choose not to participate in such subsidy/discount arrangements.

While many pharmaceutical companies are prepared to let generics compete on equal footing relative to assistance, they are unwilling to fund other direct competitors that offer drugs no different from theirs relative to price or efficacy. In fact, as shown in the following analysis, unless a manufacturer were certain that each player in the industry was doing its share, not only is the cost of assistance high but, worse, the benefits can accrue to their arch enemy or to free riders. In these cases, the system creates an incentive for the manufacturer to try to game the system in some manner to ensure that, in fact, its brand captures the majority of the subsidized prescriptions. In other cases, it dissuades many pharmaceutical companies from stepping up their contributions to support the underinsured.

Most drug manufacturers support one foundation—often one that is different from the one supported by their direct competitor. FIG. 1 shows economics of a drug manufacturer supported foundation assuming their brand has a 30% market share of new patients. This case study uses numbers fairly typical for manufacturers of biologic drugs. The analysis shows that the sponsoring manufacturer suffers a net contribution loss of $1,906 per patient. But worse still, the donor contributes $8,400 (i.e., $12,000-$3,600) in revenues per acquired patient to the competitors. Some of this would be obviously compensated back in the form subsidies from the competitor's foundation. However, to be certain of that, a drug manufacturer would have to assume that the competitor favored foundation was not gaming the system in some manner. As we know from the theory of economics, in any highly competitive industry, such indirect collusion is highly unlikely.

It was OIG's intent to create a system that does not disadvantage generic and low cost therapies, but not one where smaller share competitors are disadvantaged or that any drug manufacturer is in the uncomfortable position of helping competitors that deliver no cost benefit to the Medicare system. FIG. 2 shows that larger share competitors have greater certainty of positive contribution, for a typical manufacturer with the economic structure shown in Exhibit 1. Conversely, new market entrants, that by definition have low share, face the highest penalties in participating in foundation based programs to assist the underinsured. Once new patient market share (or in other words the share of manufacturer funding that goes towards their own brand), exceeds 50%, the foundation model becomes unconditionally viable. In even markets with modest competition, 50% or greater shares are unlikely.

The separation between the foundation and the drug manufacturer is not robust since the economic interests of the foundations and the donor are nearly completely aligned: The primary source of funding for most of the current foundations is a single pharmaceutical company per disease state. However, as discussed above, the pharmaceutical companies would be unwilling to contribute without some level of assurance that the majority, though not necessarily all of their funding, is going towards their own drugs. Hence, there is a built-in economic incentive for a foundation to "whisper in" some assurances to the manufacturer about their share of the funding in order to curry the favor of the donor and obtain increased funding.

In fact, some of the leading foundations (and their initial board member appointments) have been set up by reimbursement companies that do significant business with both the foundations they have set up and the Pharmaceutical companies. Further, there is no oversight mechanism over the foundations to ensure that no gaming goes on. Since eligibility criteria are set and interpreted by the foundations individually, without external audits, there can also be sufficient latitude to game the system in a variety of ways.

Poor patient experience, inefficiency and hence added cost in the system: Currently, it makes sense for a patient to apply to as many foundations as possible (in some cases as many as three to seven) since she cannot be sure which ones actually have funds, will approve her application, and for what amount. Each foundation has its own application process and eligibility requirements. For elderly patients, already burdened by the complexity of Part D plan choices, this is yet another daunting challenge.

The lack of uniform eligibility criteria runs counter to the OIGs desire for increased consistency and objectivity in the approval of all applications. Finally, since multiple foundations are processing applications independently for each patient, there are needless costs to the system as a whole, which ultimately detracts funds available for patients.

Further, since the foundations compete with each other for patients, there is an incentive for each foundation to make a more generous offer than the other, provided they have funding. As each foundation has its own eligibility criteria and latitude in assistance determination, and there is no standardization or audits, it is hard to tell how rampant this problem is. This can inadvertently remove the co-pay pressure on the patient and make them indifferent to even high treatment costs.

No incentive for generic manufacturers to contribute: Given their price points, generic manufacturers have no incentive to contribute to the foundations. For every branded manufacturer they end up subsidizing, the needed sales of their own generic drug will be impossibly high.

SUMMARY OF INVENTION

In accordance with one aspect of the invention, provided is a method of independently providing pharmaceutical subsidies from pharmaceutical providers to foundations. The method comprises one or more steps configured to be carried out by at least one computer system. The method includes providing a clearinghouse that maintains independence between a network of foundations and a network of pharmaceutical providers. The network of foundations is configured to submit patient requests for drugs to the clearinghouse. The network of pharmaceutical providers is configured to provide subsidies in a form including cash, in-kind drug, or a combination thereof to satisfy the patient requests. And, upon receipt of a patient request for a drug from a foundation from the network of foundations, the clearinghouse determines a subsidy to be provided by one or more of the network of pharmaceutical providers to obtain the drug and the clearinghouse directs the subsidy to the foundation.

The can further comprise determining if the drug is available from a pharmaceutical provider in the network of pharmaceutical providers.

If the drug is available from the pharmaceutical provider the method can include the pharmaceutical provider providing the subsidy in the form of only in-kind drug.

If the drug is available from the pharmaceutical provider the method can include the pharmaceutical provider providing the subsidy in the form of in-kind drug and cash.

If the drug is available from the pharmaceutical provider the method can include establishing a fair market value of the drug by the pharmaceutical provider providing at least a portion of the subsidy in the form of cash and procuring the drug on the open market with the cash.

If the drug is not available from any pharmaceutical provider in the network of pharmaceutical providers, the method can include determining an amount needed to procure the drug and determining a cash portion of the amount to be paid by one or more of the pharmaceutical providers in the network of pharmaceutical providers.

Determining the cash portion can include determining a pro rata portion to be paid by each of the one or more pharmaceutical providers, which can include determining the pro rata portion as a function of the total amount of all subsidies provided by the network of pharmaceutical providers.

The method can include the patient submitting a single application and a plurality of foundations competing to provide obtain the subsidy and provide the drug to the patient.

The method can further comprise establishing a low-cost pharmaceutical provider threshold, whereby pharmaceutical providers that provide drugs that cost less than the low-cost threshold do not subsidize pharmaceutical providers having drugs that costs more than the low cost threshold.

The method can further comprise establishing a low-cost pharmaceutical provider threshold, whereby pharmaceutical providers that provide drugs that cost less than the low-cost threshold provide subsidies in a smaller proportion than pharmaceutical providers having drugs that cost more than the low cost threshold.

The method can comprise using a uniform and auditable standard of patient need assessment to determine eligibility for and the amount of subsidy.

The method can further include providing the subsidy in the form of one or more coupons that can be applied against the drug costs and patient co-pay for any drug in a given disease state.

In accordance with another aspect of the invention, provided is a pharmaceutical clearinghouse system, configured to independently provide pharmaceutical subsidies from pharmaceutical providers to foundations. The system comprises a clearinghouse configured to maintain independence between a network of foundations and a network of pharmaceutical providers. The network of foundations is configured to submit patient requests for drugs to the clearinghouse. The network of pharmaceutical providers is configured to provide subsidies in a form including cash, in-kind drug, or a combination thereof to satisfy the patient requests. And the system also includes a set of subsidy modules configured, upon receipt of a patient request for a drug from a foundation from the network of foundations, to determine a subsidy to be provided by one or more of the network of pharmaceutical providers to obtain the drug and to direct the subsidy to the foundation.

The system can further comprise an intake processor configured to determine if the foundation is in the network of foundations.

The set of subsidy modules can be configured to determine if the drug is available from a pharmaceutical provider from the network of pharmaceutical providers and, if so, to request the subsidy from the pharmaceutical provider in the form of only in-kind drug.

The set of subsidy modules can be configured to determine if the drug is available from a pharmaceutical provider from the network of pharmaceutical providers and, if so, to request the subsidy from the pharmaceutical provider in the form of only in-kind drug and cash.

The set of subsidy modules can be configured to determine if the drug is available from a pharmaceutical provider from the network of pharmaceutical providers and, if so, to establish a fair market value of the drug by requesting the pharmaceutical provider to provide at least a portion of the subsidy in the form of cash to enable procurement of the drug on the open market with the cash.

The set of subsidy modules can be configured to determine if the drug is available from a pharmaceutical provider from the network of pharmaceutical providers and, if not, to: determine an amount needed to procure the drug; and determine a cash portion of the amount to be paid by one or more of the pharmaceutical providers in the network of pharmaceutical providers.

The set of subsidy modules can be configured to determine a pro rata portion of the cash portion to be paid by each of the one or more pharmaceutical providers, as a function of the total amount of all subsidies provided by the network of pharmaceutical providers.

The clearinghouse can be configured to enable a plurality of foundations to compete to obtain the subsidy and provide the drug to the patient based on a single patient request.

The clearinghouse can configured to establish a low-cost pharmaceutical provider threshold. And the set of subsidy modules can be configured to determine the subsidies such that pharmaceutical providers that provide drugs that cost less than the low-cost threshold do not subsidize pharmaceutical providers having drugs that cost more than the low cost threshold.

The clearinghouse can be configured to establish a low-cost pharmaceutical provider threshold. And the set of subsidy modules can be configured to determine the subsidies such that pharmaceutical providers that provide drugs that cost less than the low-cost threshold provide subsidies in a smaller proportion than pharmaceutical providers having drugs that cost more than the low cost threshold.

The clearinghouse can be configured to establish a uniform and auditable standard of patient need assessment to determine eligibility for and the amount of subsidy.

The clearinghouse can be configured to provide the subsidy in the form of one or more coupons that can be applied against the drug costs and patient co-pay for any drug in a given disease state.

BRIEF DESCRIPTION OF THE DRAWINGS

The drawing figures depict preferred embodiments by way of example, not by way of limitations. In the figures, like reference numerals refer to the same or similar elements.

FIG. 1 is a table showing a prior art example of typical drug manufacture economics.

FIG. 2 is a table showing an example of market share information that could be used by the clearinghouse for determining pro rata shares of contributions by registered pharmaceuticals for pharmaceuticals offered by unregistered pharmaceutical providers.

FIG. 4 is a table showing a clearinghouse example where registered providers contribute toward drugs offered by out of network providers.

FIG. 5 is a table showing a clearinghouse example involving a low-cost provider.

DETAILED DESCRIPTION OF PREFERRED EMBODIMENT

A pharmaceutical clearinghouse establishes relationships with a set of foundations and a set of pharmaceutical providers. A foundation, as used herein, can be a charity, a third-party independent of the pharmaceutical providers, or any other entity recognized by the OIG as able to serve such role, in the present context. A pharmaceutical provider, as used herein, can be a drug company or manufacturer or other entity recognized by the OIG as able to serve such role, in the present context.

In response to the clearinghouse receiving a patient request for a pharmaceutical from a foundation, the clearinghouse obtains a subsidy from at least one provider and provides or otherwise directs the subsidy to the foundation. Systems, methods and computer program products can implement the clearinghouse in a variety of forms, without departing from the present invention. The subsidy can be cash, in-kind drug, or a combination thereof. What follows is one possible embodiment of various aspects of the present invention.

The current model for assisting the under-insured relies on a single "black-box", namely a foundation, to separate the patient from the donor pharmaceutical provider. To address the problems with this model, one needs to have two "black boxes" in tandem between the patient and the pharmaceutical provider, to make the system of giving and receiving assistance "double-blind." Additionally, to address efficiency and effectiveness concerns, the second "black-box" should also function as a clearinghouse, much as MasterCard/Visa serve the credit card industry and Galileo/Sabre serve the travel industry.

Figure 3:
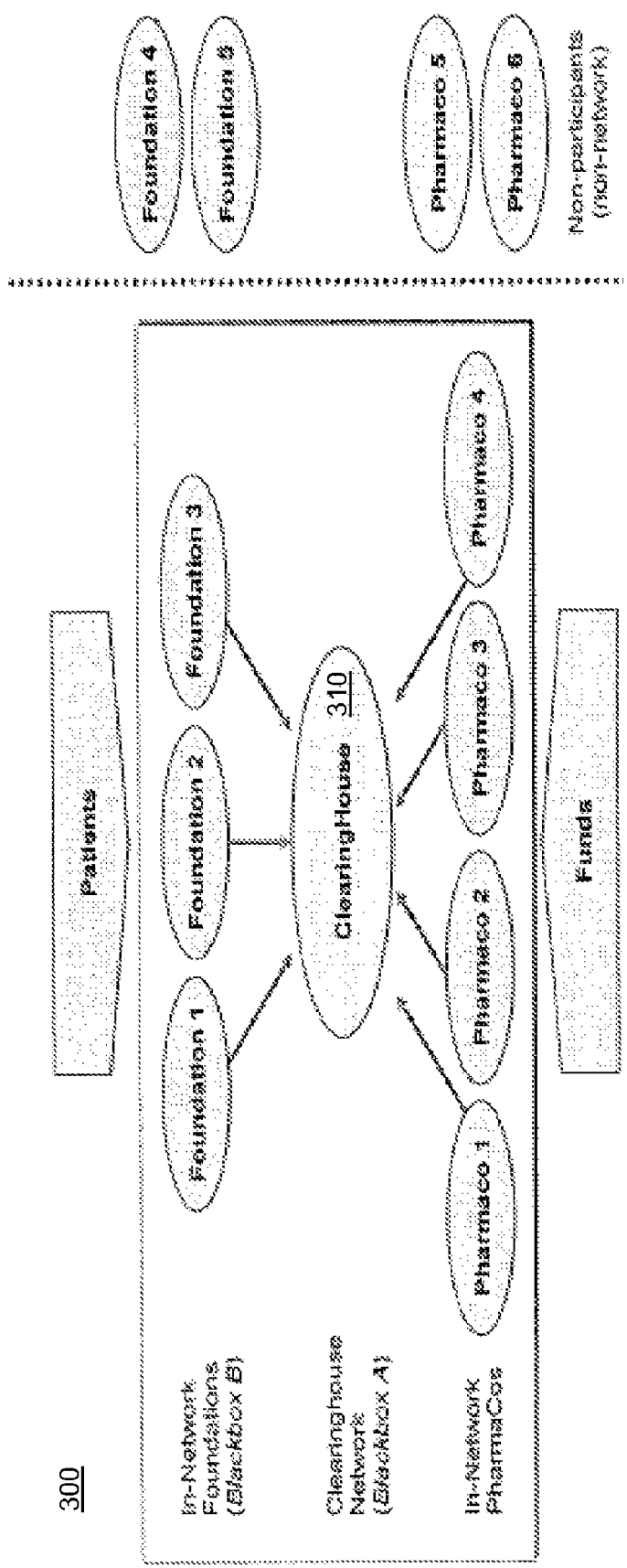
FIG. 3 is a block diagram of a clearinghouse model in accordance with the present invention.

An embodiment of the clearinghouse model is shown in FIG. 3. In the proposed model 300, participating pharmaceutical providers (such as Pharmacos 1-4) funnel all of their funds for at least one disease state (e.g., rheumatoid arthritis, diabetes, Alzheimers, and so on) through at least one clearinghouse 310, which in turn allocates and passes along the funds to all enrolled foundations, such as Foundation 1, Foundation 2, and Foundation 3. The foundations continue to deal with patients as they currently do, but no longer receive direct funding from the pharmaceutical providers. Each foundation sends its applications to the clearinghouse 310 and receives subsidies, e.g., full or partial funding, the pharmaceutical, or a combination thereof, to address patient requests.

In the exemplary embodiment, each participating provider (such as Pharmacos 1-4) fully funds (via the clearinghouse) all patients that are prescribed the provider's brand, but also contributes an allocated share of funds to cover all of the other patients requesting drugs provided by non-participating providers (e.g., such as Pharmaco 5 and Pharmaco 6). In one embodiment, the clearinghouse 310 is implemented such that the participating ("in-network") pharmaceutical providers know exactly how much of their funding was used on their own drugs. Thus, the in-network pharmaceutical providers would neither be able to favor any one foundation over the other nor have anything material to gain from doing so. Also, the information would be likely the same as, or at least consistent with, that computable from publicly available market share information of known in-network pharmaceutical providers.

In the preferred form, each patient needs only to apply to one foundation of their choice. This eliminates duplicate processing caused when patients apply to multiple foundations. The clearinghouse 310 treats each foundation substantially the same—it preferably does not favor one foundation over another.

Role of the Foundation: The foundation is responsible for making uninsured or underinsured patients aware of its services, processing their applications, and disbursing funds with complete disregard for the prescribed brand. That is, in the preferred form, the foundation should not favor one pharmaceutical provider over another. Patients can work with any one foundation of their choice based on their perception of its quality of service. The amount of funding approved for the patient from one foundation to the next will be substantially the same—because each patient request is preferably honored by the clearinghouse, regardless of the foundation that submitted it. While a foundation may canvas pharmaceutical providers to contribute funds for current and future disease states, which it should as an advocate of patient care, all funds would flow through (or under the direction of) the clearinghouse to all enrolled foundations, and not just the canvassing foundation. If a foundation wished to increase its funding it simply would need to attract and process more patients, regardless of the brand of product they were prescribed. The foundation does not have any direct relationships or arrangements with the in-network pharmaceutical providers—and in the preferred form the foundations would not receive any funds directly from an in-network pharmaceutical provider for a given disease state, unless under the direction of the clearinghouse.

Role of the Clearinghouse: The clearinghouse is responsible for informing participating pharmaceutical providers (e.g., drug manufacturers) of their allocated share of the needed funds, and then collecting and disbursing (or otherwise directing) the funds appropriately to each foundation. In the preferred embodiment, funds are not to any patients directly, but in various other embodiments it can be allowed to provide assurances and accountability. Additionally, the clearinghouse could host a number of shared processes to increase efficiencies (e.g., lower cost, improve response time, etc.) and enforce standardization.

How the process works—Preferred Embodiment: Typically, a patient prescribed a particular brand of drug calls the reimbursement hotline offered by the brand, i.e., pharmaceutical provider. The reimbursement agent from the provider evaluates the patient's insurance and advises the patient of its payment burden. If the patient is unable to meet her co-pay, the reimbursement agent typically provides the patient names and contact information of a number of foundations that can offer assistance relative to the patient's drug need.

The foundations can "compete" with each other for the patient's "business" based on the quality of their support services and speed of response, as examples. The patient will pick one foundation, say, Foundation 1, and give it written authorization to process her application. The authorization request will contain basic information—the patient's name, social security number, and prescribed brand of drug for which assistance is needed. Foundation 1 will inform the clearinghouse, thus preventing other Foundations 2 and 3 from also needlessly processing that same application, in the event the patient also authorizes them to do so. The first foundation to send a valid reservation (or patient request) gets to process the patient's request.

In the illustrative embodiment, the clearinghouse will furnish Foundation 1 with a standardized application for the disease state covering the requested brand. Foundation 1 will have a period of time (e.g., 4 weeks) to complete the financial diligence and approve the application. It can be implemented so that it is permissible for the foundation to apply for an extension on its patient reservation, if necessary, with the patient's written authorization. Given a standardized application criteria and methodology, the amount of financial assistance from one foundation to the next will not vary significantly. Upon completion of the application, the foundation will inform the clearinghouse of the amount of assistance and the clearinghouse will disburse it. In general, the clearinghouse will not collect or review the applications and the only information it will have, in this embodiment, is the patient's social security number, brand of drug prescribed, and the amount of financial assistance required for such patient requested pharmaceutical.

At the end of each month, the clearinghouse can compute the ratio of the total funds disbursed across all brands to and by all participating foundations for a given disease state versus the total funds needed to cover the brands of the in-network pharmaceutical providers. For example, if the disease state is rheumatoid arthritis and the clearinghouse and foundations disbursed $138K for bands offered by participating+non-participating pharmaceutical providers, with $100K for brands offered by participating pharmaceutical providers for the disease state, then the ratio is $138K/$100K, which is 138%. Next, each pharmaceutical provider would be asked to fund fully the amount needed to cover its brand plus the percentage needed to cover non-participating (or out-of-network) pharmaceutical providers brands (i.e. the 38% or $38K).

FIG. 3 illustrates how the clearinghouse 310 works in this embodiment. The extra $38K can be divided among the participating pharmaceutical providers in any of a variety of manners. But in the preferred embodiment, each provider pays a pro rata share of the $38K. So, if Pfizer, Inc. was a participating provider and disbursed $25K for its own drug (i.e., out of the $100K), then Pfizer would pay 25% of the $38K, and so on.

Other Aspects of the Illustrative Preferred Embodiment:

In various embodiments, the clearinghouse 310 will set uniform criteria for enrolling foundations, in what can be considered a network of foundations. Pharmaceutical providers will have no involvement in the enrollment process. Generally, all foundations that offer competitive costs and quality of service will be allowed to join the network. Examples of situations in which a foundation is not allowed to join the network can include one or more of the following: the foundation's administrative charges are significantly higher than the norm relative to others in the network; the foundation has been set up to assist just 1-2 patients when the norm for others is much greater (e.g., 500+); the foundation has been found to repeatedly violate the required processes for evaluating patient need and eligibility; the foundation has been found to or is reasonably believed to have engaged in unethical or illegal conduct, etc. However, as a general matter, the clearinghouse 310 will, in most instances, be inclined to enroll more, not fewer foundations.

In various embodiments, the clearinghouse 310 preferably has no role in evaluating patient applications or determining the amount of assistance. The clearinghouse merely matches subsidies (e.g., cash or in-kind drug) efficiently to the foundations that request the assistance. The foundations will bear the responsibility, as they currently do, for attracting, evaluating, processing, and approving patient applications per standardized criteria. The foundations then disburse their subsidies received via the clearinghouse 310.

In various embodiments, eligibility criteria for privately insured patients will be designed to be the same or similar to those used for Medicare patients, except where disallowed by existing contracts with such insurers. Specifically, they will generally not be more generous towards Medicare patients. This ensures that the cost control pressures that private insurers apply towards their own patients (e.g. up-tiering generics, requiring prior-authorizations, or failure of lower costs therapies first, etc.) are equally felt by Medicare patients subsidized by the United States Federal government.

In various embodiments, the eligibility criteria will consider income and assets for patients requiring acute therapy and income and available annual cash-flow for chronic therapies. Hence, such criteria can cover income, local cost of living, family size, expenses, scope and extent of patient medical bills, co-pay gap versus current payments, etc. The criteria can be somewhat different by disease state, i.e. more generous for high cost therapies. To ensure that patients are only receiving funding to the level they need and not needlessly eliminating cost pressures, the application will be reasonably thorough.

In various embodiments, the clearinghouse 310 and the pharmaceutical provider will have no direct contact with the patients in the processing their application.

In various embodiments, the foundations and patients will receive no direct funds for the disease state from the pharmaceutical provider (e.g., drug manufacturer).

In various embodiments, the foundations will disburse assistance purely on the basis of patient financial need, without regard to the brand prescribed.

In various embodiments, participation in the clearinghouse model 300 by pharmaceutical providers and the foundations is entirely voluntary. Preferably, for any given disease state the pharmaceutical provider (e.g., drug manufacturer) can provide assistance directly to an in-network foundation or through the clearinghouse 310, but not both simultaneously in a given balance of calendar year.

In various embodiments, assistance to existing patients in all of the in-network foundations will also flow through the clearinghouse 310 in the future to simplify transaction processing and lower system costs. Patients themselves will see no difference in their interactions since they will continue to deal with the foundation with which they currently work. However, they will be required to give permission to the foundation to transfer the required information to the clearinghouse 310 as a condition for future continuation of funding. Most foundations already require patients to re-qualify annually and this would be added to all future re-qualification requests.

In various embodiments, the clearinghouse 310 can require all in-network pharmaceutical providers to provide sufficient funding to cover all patients—i.e. the "house" will always fully "clear." There can be unforeseen situations in which for one reason or another a pharmaceutical provider is unable to meet its full financial commitment. In those situations, its brand's share of the patients could be proportionally reduced, the house will not fully clear and there will be a waiting list.

Some of the issues with the current foundation model that are addressed by the illustrative embodiment of a clearinghouse model 300 include:

More robust compliance with the OIG intent: In various embodiments, the pharmaceutical providers have no direct transactional relationship with the in-network foundations, unless directed or managed by or through the clearinghouse 310. Further, the pharmaceutical provider is indifferent as to which foundation actually disburses the funds to the patients, so long as the foundation's administrative charges are competitive. The foundation, in turn, is indifferent as to the source from which clearinghouse 310 secures its funding, since all approved patients are provided the requested assistance. The foundation does have an interest in growing its business and the only way for it to do so is by securing additional patients regardless of the prescribed brand.

Further, given the preferred standardization of application processing, the clearinghouse model 300 better complies with the OIG's desire for a reasonable, verifiable, and uniform process for assessing patient financial need.

Economic context that supports increasing funding from providers: In various embodiments, the clearinghouse model 300 eliminates the ability of pharmaceutical providers (e.g., drug manufacturers) to game individual foundations and ensures that all in-network pharmaceutical providers share the burden of non-participating pharmaceutical providers evenly. Hence, the pharmaceutical providers are assured that they are in effect providing their drugs to the underinsured patients at a discount and not a loss.

FIG. 4 provides a table showing an example of financial implications for a set of Foundations A-D using the clearinghouse model 310 of FIG. 3. In FIG. 4, we see that these discounts can be generous and, in the illustrative case, at 41% (i.e., for providers of Brand X and Brand Z). Also we note that the share of funding of contributing pharmaceutical providers (i.e., for Brand X and Brand Z) applied towards their own brands is 73%, which as we see from FIG. 4 is sufficient to ensure there is a modest, but positive variable contribution from the providers.

Better patient experience: In various embodiments, the foundations, in effect, will compete for the patients by reaching them first, creating awareness of their programs, and providing excellent service and hand-holding. Further, the patients will need to apply to only one foundation and deal with a single eligibility criteria. Since the system creates a context that encourages pharmaceutical providers to increase funding, fewer patients will need to wait in queues and delay their therapies.

Resource efficiency: In various embodiments, the clearinghouse 310 will help to reduce waste by eliminating the need for multiple foundations to process the same patient applications. Assuming the average patient applies to three (3) foundations, this will cut down the system-wide application processing workload by two-thirds.

Variations to the Clearinghouse Model

Audit of patient applications: In various embodiments, to ensure that the foundations are applying a uniform and fair standard to every patient application, the clearinghouse 310 can audit patient applications, for example, following statistical random sampling methodology. Foundations with a poor record of compliance can be sanctioned in a number of ways, including, as possible examples, such control methods as requiring staff to undergo re-training and/or imposing fines.

Inform CMS (Centers for Medicare and Medicaid Services) COB (Coordination of Benefits) of financial assistance: In various embodiments, the clearinghouse 310 can transmit to the pharmaceutical providers information indicating the cash assistance approved for the participating foundation patients. For example, the clearinghouse 310 could transmit a single file daily of all cash assistance approved for the participating foundation patients. This will make communication of the benefits to plan easier for CMS.

Allow pharmaceutical providers to contribute in cash or in-kind: In various embodiments, the in-network pharmaceutical providers can provide patients that have been prescribed their drug with free drug up to the value of the approved assistance level. The in-network pharmaceutical providers can still be required to provide cash assistance to patients prescribed brands of other, non-participating pharmaceutical providers. In the example in FIG. 4, Brand Z can supply its 400 patients with, in effect, $1.6M in free drug. However, it must still pay the balance $600,000 in cash to meet its clearinghouse 310 commitment of $2.2M and support low cost Brand Y, which does not participate in the network. Since the foundations can award assistance to patients without regard to the brand prescribed, and all foundations can provide free drug, this does not create any kind of tie in. It does improve the ability of a pharmaceutical provider to use its funds more efficiently, since free drug distribution usually avoids royalty payments which for many drugs can be equal to the costs of goods sold. The product distribution to the patient would be contracted by the clearinghouse 310 with potentially third-party vendors that could take shipment orders directly from any of the in-network foundations.

Allow low-cost/generic drug manufacturers to not subsidize high-cost/branded drugs: In various embodiments, to encourage low cost and generic drug manufacturers to participate in programs for the under-insured, the clearinghouse 310 can require that a given pharmaceutical provider needs to only subsidize its own drug and any that are no more than 20% more expensive, for example. Hence, generic drug manufacturers that sell their brands at substantial discounts do not need to contribute funds towards higher priced brands even when the physician prescribes those to the patient. This will remove a key barrier from their willingness to contribute to the system. This is illustrated in the revised scenario in FIG. 5, where the low cost Brand Y only pays its own share of the funding (plus that of other non-participating lower cost drugs if there were any), and the burden of supporting premium priced Brand Z falls entirely on Brand X.

Extend Clearinghouse Model to serve institutional Patient Assistance Programs (PAPs): In various embodiments, many of the issues that institutional PAPs face can also be resolved by inserting a clearinghouse 310 between the pharmaceutical provider and the hospitals. In this sense, the hospitals are replacing the "501(c)3" foundations in the model above. For example, this would sever any possible link between the amounts of assistance received by a given hospital from any contract negotiations a pharmaceutical provider has with the hospital on the use of the pharmaceutical provider's brand. Participating hospitals can be included in the clearinghouse model 300 based on a set of uniform criteria and the pharmaceutical providers need not have any say in the matter. Drug replenishment would be based on tracked patient use. Safeguards already adopted by hospitals against brand steering would continue to apply as is currently done (e.g. no advertising, prescription before assistance, etc.). Patient acceptance criteria would also be standardized by disease state across all hospitals, applications periodically audited for compliance (e.g., statistical random sample) and the assistance would be available to the patient through any participating hospital and not conditioned on the use of other services. In other words, the way for the hospital to earn the patient's business would be by advocating its standard of care and not on the assistance. In fact, once the patient and his approved assistance level has been recorded in the clearinghouse 310 by one hospital, the patient could pick up the drugs at any hospital up to the limit of their assistance with the clearinghouse 310 tracking the total amount. Further separation between the hospital and patient can be achieved by having all patients apply to a designated foundation that processes and approves the assistance. The product inventories can be held in contingency at the hospital and replenished in bulk periodically.

Figure 6:
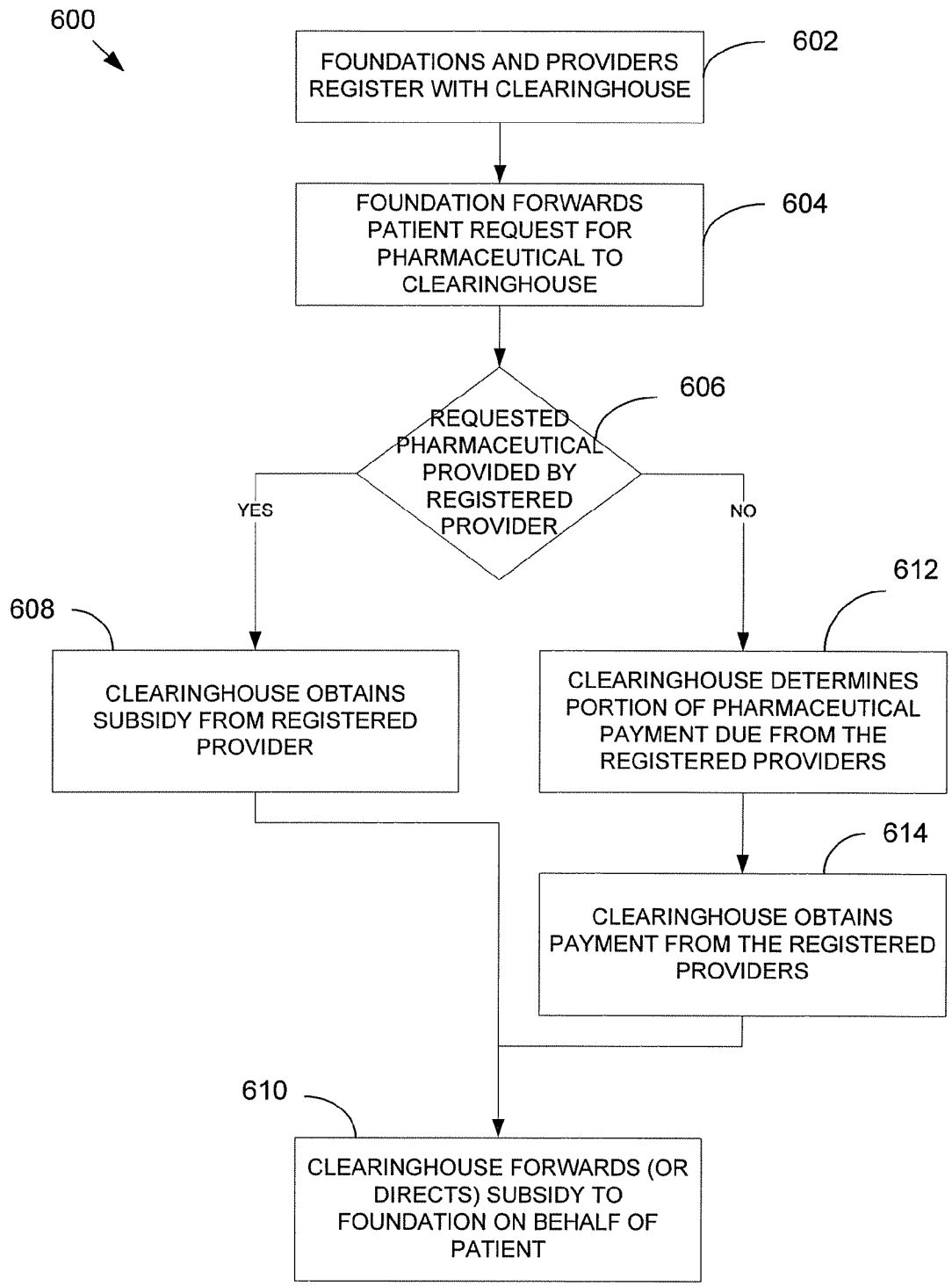
FIG. 6 is a flowchart showing a method of providing a clearinghouse.

FIG. 6 shows a top level flowchart of a method of providing a clearinghouse 310. In step 602 foundations and pharmaceutical providers register with the clearinghouse 310, which could be considered to form a network of foundations, a network of pharmaceutical providers, or a network comprising the foundations, the clearinghouse 310 and the providers. In step 604, a foundation that has received a patient's request for a drug forwards that request to the clearinghouse 310. In step 606, the clearinghouse 310 determines whether or not an in-network pharmaceutical provider provides the requested drug. If an in-network pharmaceutical provider does provide the drug, then the process continues to step 608, where the clearinghouse 310 obtains in-kind drug from the in-network pharmaceutical provider, or could obtain cash to buy the drug on the open market, or could obtain a combination of the foregoing—all as forms of a subsidy.

If the drug is not provided by an in-network pharmaceutical provider, then the process continues to step 612 where the clearinghouse 310 determines the necessary payments to be obtained from the in-network pharmaceutical providers needed to purchase the drug from the appropriate out-of-network pharmaceutical provider, or otherwise on the open market. In some embodiments, if an in-network pharmaceutical provider is a low-cost provider (e.g., a generic drug company) of a similar drug for the same disease state and if the cost of the requested drug is above a threshold amount relative to the cost of the low-cost pharmaceutical provider's drug (e.g., 20% more expensive) then the low-cost provider need not be required to contribute anything, or possibly a reduced amount, to the cost of the requested pharmaceutical. In step 610, the clearinghouse 310 provides or otherwise directs the subsidy, whether in-kind drug, cash, or a combination thereof, to the foundation to fulfill the patient's request.

Figure 7:
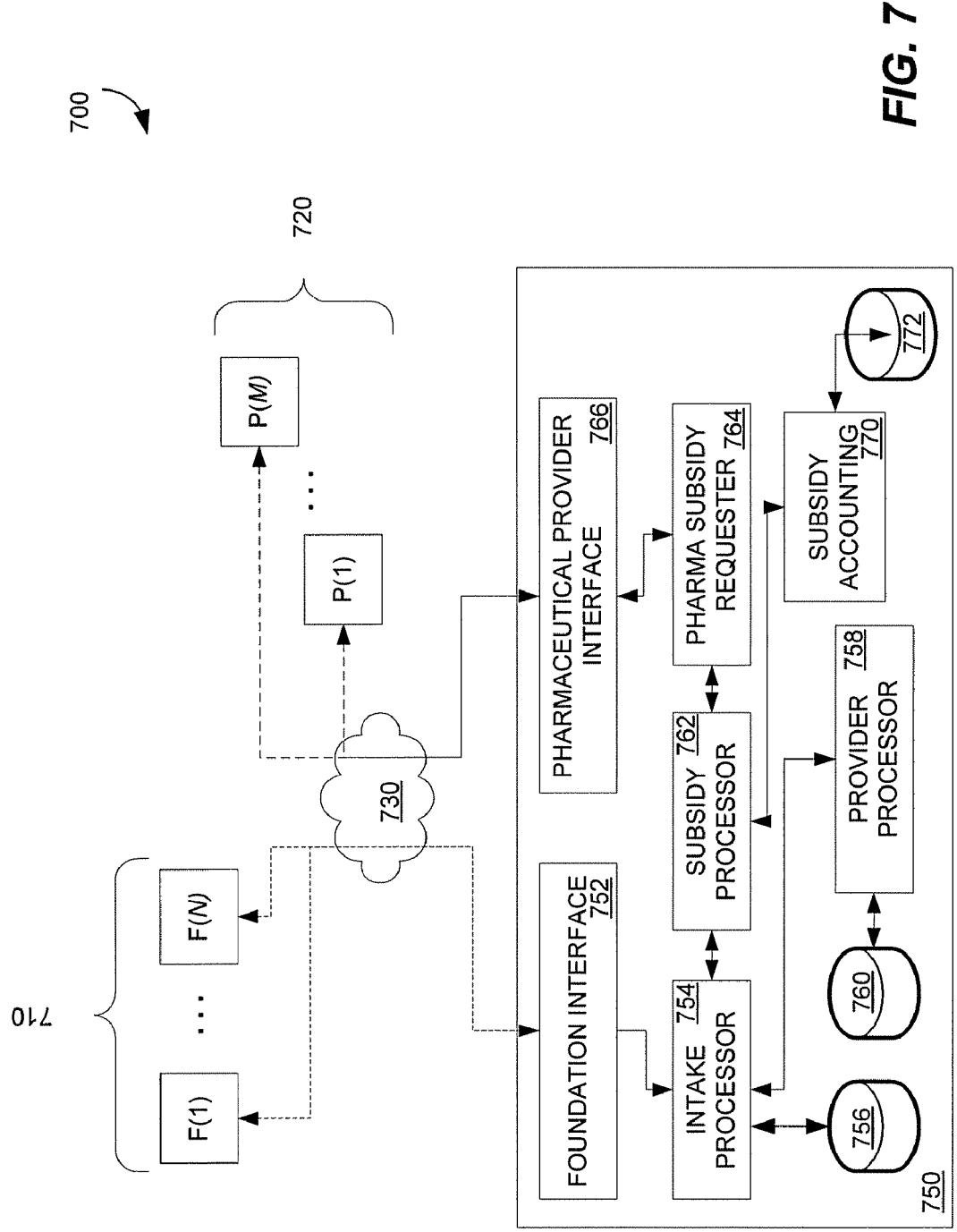
FIG. 7 is a block diagram example of a computer system that can be used to implement a clearinghouse method.

FIG. 7 is a block diagram example of a computer system 700 that can be used to implement a clearinghouse method, such as that of FIG. 6. In this embodiment, system 700 shows a set of foundations F(1)-F(N) 710 that can register with a clearinghouse system 750, and become in-network foundations 710. A set of pharmaceutical providers P(1)-P(M) 720 can also register with clearinghouse system 750, and become in-network pharmaceutical providers 720. The in-network foundations 710 and the in-network pharmaceutical providers 720 can interact with clearinghouse system 750 over any of a variety of types of wired or wireless networks, or combinations thereof—collectively represented as network cloud 730. The networks can include the Internet, World Wide Web, local area networks, wide area networks, virtual private networks, or the like, and any combination thereof.

In various embodiments, clearinghouse system 750 can comprise a set of functional modules that can be implemented in hardware, software, firmware or some combination thereof. In this embodiment, a foundation interface 752 facilitates interaction between the foundations 710 and clearinghouse system 750, and can implement a set of login or security functionality for secure access by the in-network foundations 710. Foundation interface 752 also allows the submission of patient requests (e.g., approved applications) for a drug. The drug is ultimately subsidized by one or more of the in-network pharmaceutical providers 720. An intake processor 754 accesses a system database 756 that includes information about the in-network foundations 710 and determines if the requesting foundation is indeed registered and in the network. If the requesting foundation is not, the intake processor 754 can reject the request.

If the requesting foundation is an in-network foundation (i.e., a registered with clearinghouse system 750) then the intake processor 754 tasks a provider processor 758 to determine if an in-network pharmaceutical provider 720 makes the requested drug—this can require checking a database 760 that includes a list of in-network pharmaceutical providers to see if one of them is the maker of the requested drug and/or accessing external databases and systems (not shown). The intake processor 754 then passes the request to a subsidy processor 762, along with an indication of the pharmaceutical provider of the requested drug, whether in-network or out-of-network.

If the requested drug is provided by an in-network pharmaceutical provider 720, then a pharma subsidy requester 764 prepares a request to the specific pharmaceutical provider to provide the subsidy. The subsidy processor 762 or pharma subsidy requester can determine or obtain the market value of that in-kind drug subsidy. However, if the requested drug is not provided by an in-network pharmaceutical provider 720, then the subsidy requester 764 determines the cost of the requested drug (which can be obtained from external sources) and determines the amount of cash contribution (or subsidy) due from each in-network pharmaceutical provider to procure the requested drug. The pharama subsidy requester 764 can also be configured to task the in-network pharmaceutical providers to contribute their respective portions of the subsidy, whether cash, in-kind drug, or a combination thereof. The pharama subsidy requester 764 can interact with the providers via a pharmaceutical provider interface 766 and network 730.

A subsidy accounting module 770 can be provided that stores and tracks the required subsidies to be made by each of the in-network providers 720 and can track which of the foundations 710 received which subsidies. The subsidy accounting module 770 can also track the subsidies to each patient. This information can be stored in accounting database 772. The subsidy accounting processor 770 can also track subsidy payments from the in-network pharmaceutical providers 720 against the amount they owe. The subsidy accounting processor 770 can also can determine the totals and relative percentages of subsidies allocated to each in-network pharmaceutical provider and perform the tasks and calculations described with respect to FIGS. 4 and 5 above.

The clearinghouse system 750 can include modules for allowing or enabling on-line or electronic submission of patient requests by foundations though a browser-based interface, as an example. Similarly, a browser-based interface can be provided for the in-network pharmaceutical providers, which can allow insight into financial information related to their subsidies, such as totals and percentage relative to all other in-network pharmaceutical providers. Clearinghouse system 750 can also include electronic payment of funds (or electronic funds transfer) functionality for enabling quick and efficient payment of subsidies by the in-network pharmaceutical providers, this could be implemented as part of subsidy accounting module 770. All of this could be implemented relative to specific disease states, or more generally.

The platforms used to host the above functional modules can be typically available personal computers, workstations, laptops, servers and the like. The system could be accessible by any of a variety of wired or wireless devices, or a combination thereof, including, but not limited to personal digital assistants and cellular telephones. The communications equipment, paths, interfaces, and protocols can be any appropriate in the prior art, so not discussed in detail herein.

In various embodiments, the clearinghouse can be implemented to provide all or some subsidies as free drug, as noted above. In the case of providing free drug, the clearinghouse can facilitate the acquisition on the open market of a drug offered by a non-participating pharmaceutical provider with the cash subsidies provided by the in-network pharmaceutical providers. In some embodiments, a portion (e.g., 25%) of the drugs of the in-network providers can also be acquired on the open market for purposes of, for example, establishing a price threshold for TrOOP valuations. The methods and systems described herein can also be adapted to use part cash and part drug for all pharmaceutical providers. And in-network pharmaceutical providers could be given the option of donating their drug when requested or donating a cash subsidy.

For lower cost drugs, the clearinghouse can work in a modified manner. For example, eligible patients can be provided universal coupons that can be applied against their drug costs and co-pays. The coupon will be valid for any drug in a given disease state. Disbursement agents can qualify patients using uniform criteria. The cost of couponing can be shared by in-network pharmaceutical providers, e.g., using the pro-rata share methodology, including the funding burden for out-of-network pharmaceutical providers.

While the foregoing has described what are considered to be the best mode and/or other preferred embodiments, it is understood that various modifications can be made therein and that the invention or inventions can be implemented in various forms and embodiments, and that they can be applied in numerous applications, only some of which have been described herein. For example, while the embodiments focus on pharmaceuticals, it could be implemented for any of a variety of patient therapies. As used herein, the terms "includes" and "including" mean without limitation. It is intended by the following claims to claim any and all modifications and variations that fall within the true scope of the inventive concepts.

What is claimed is:

1. A method of independently providing subsidies, in the form of cash, drugs as an in-kind subsidy or a combination of cash and drugs, from pharmaceutical providers to patients via foundations, the method comprising:

provinding a computer-based clearinghouse system having a processor coupled to a data storage device and a network connection to enable communication with external computer systems over at least one network;

defining in the data storage device a network of foundations and a network of pharmaceutical providers;

receiving a request for a drug within a given and defined disease state from a foundation by the clearinghouse system, on behalf of a patient who has been prescribed that drug by a physician, from the network of foundations;

in response to the request, determining and requesting a subsidy to be provided by one or more pharmaceutical providers that have agreed to participate in providing subsidies for any drug prescribed within the pre-defined disease state from the network of pharmaceutical providers by the clearinghouse system;

directing the subsidy to the foundation as a response to the request by the clearinghouse system; and the clearinghouse system maintaining an accounting of portions of the subsidy provided by each of the one or more of the participating pharmaceutical providers, wherein the subsidy can include the requested drug, cash, or some combination thereof, wherein the pharmaceutical provider has no influence or control over setting of the program rules by which the subsidy is disbursed in a given disease state, wherein, the rules for the determination of the eligibility of a patient for subsidy and the amount and form of subsidy are based on a uniform criteria, which are based on defined measures of patient financial need including annual income below a multiple of the federally defined poverty level, set by the clearinghouse across all foundations participating in the clearinghouse network, wherein the pharmaceutical providers contributions are not conditional on only their own brand of drug being prescribed to the patient or only their choice of a provider or specific pharmacy being used, wherein the requested drug may or may not be manufactured by the pharmaceutical providers participating in the network, wherein the burden of supporting brand of drugs manufactured by non-participating pharmaceutical providers is shared by the participating pharmaceutical providers in a manner proportional to the benefit derived by the pharmaceutical provider in the form of its own drug subsidies through the clearinghouse relative to the other pharmaceutical participants, wherein there is no data exchange between the clearinghouse and the pharmaceutical provider or between the foundations and pharmaceutical providers that allows pharmaceutical subsidy providers to correlate their donations to the number of prescriptions subsidized by a charity, and wherein the giving and receiving of the subsidy is double-blind, so that the one or more pharmaceutical providers do not know which foundation requested and patient received the subsidy, and the foundation and patient do not know which one or more pharmaceutical providers provided the subsidy.

2. The method of claim 1, further comprising:
determining if the drug is available from a pharmaceutical provider in the network of pharmaceutical providers.

3. The method of claim 2, wherein if the drug is available from the pharmaceutical provider, the method including:
the clearinghouse system requesting the pharmaceutical provider to provide the subsidy in the form of only the drug.

4. The method of claim 2, wherein if the drug is available from the pharmaceutical provider, the method including:
the clearinghouse system requesting the pharmaceutical provider to provide the subsidy in the form of the drug and cash.

5. The method of claim 2, wherein if the drug is available from the pharmaceutical provider the method including:
establishing a fair market value of the drug by the pharmaceutical provider providing at least a portion of the subsidy in the form of cash and procuring the drug on the open market with the cash.

6. The method of claim 1, wherein if the drug is not available from any pharmaceutical provider in the network of pharmaceutical providers, the method including:
determining an amount needed to procure the drug; and
determining a cash portion of the amount to be paid by one or more of the pharmaceutical providers in the network of pharmaceutical providers.

7. The method of claim 6, wherein determining the cash portion includes the clearinghouse system determining a pro rata portion to be paid by each of the one or more pharmaceutical providers, including determining the pro rata portion as a function of the total amount of all subsidies provided by the network of pharmaceutical providers.

8. The method of claim 1, including:
if the clearinghouse system receives multiple requests for the same drug for the same patient from a plurality of foundations, the clearinghouse system selecting only one of the multiple requests for receipt of the subsidy.

9. The method of claim 1, further comprising:
the clearinghouse system establishing a low-cost pharmaceutical provider threshold, whereby pharmaceutical providers that provide drugs that cost less than the low-cost threshold do not subsidize pharmaceutical providers having drugs that cost more than the low-cost threshold.

10. The method of claim 1, further comprising:
the clearinghouse system establishing a low-cost pharmaceutical provider threshold, whereby pharmaceutical providers that provide drugs that cost less than the low-cost threshold provide subsidies in a smaller proportion than pharmaceutical providers having drugs that cost more than the low-cost threshold.

11. The method of claim 1, further comprising:
the clearinghouse system applying a uniform and auditable standard of patient need assessment to determine eligibility for and the amount of the subsidy.

12. The method of claim 1, further including:
providing the subsidy in the form of one or more coupon that can be applied against the drug costs and patient co-pay for any drug in a given disease state.

13. A pharmaceutical clearinghouse system, configured to independently provide subsidies in the form of cash, drugs as an in-kind subsidy or a combination of cash and drugs, from pharmaceutical providers to foundations, the system comprising:

a network connection to enable communication with external computer systems over at least one network;

a computer storage device having stored therein information identifying a network of foundations and a network of pharmaceutical providers; and at least one clearinghouse processor configured to:

receive a request for a drug within a given and defined disease state from a foundation, on behalf of a patient who has been prescribed that drug by a physician, from the network of foundations;

in response to the request, determine and request a subsidy to be provided by one or more pharmaceutical providers that have agreed to participate in providing subsidies for any drug prescribed within the pre-defined disease state from the network of pharmaceutical providers, while maintaining anonymity of the foundation;

direct the subsidy to the foundation as a response to the request; and maintain an accounting of portions of the subsidy provided by each of the one or more of the participating pharmaceutical providers, wherein the subsidy can include the requested drug, cash, or some combination thereof, wherein the pharmaceutical provider has no influence or control over setting of the program rules by which the subsidy is disbursed in a given disease state, wherein, the rules for the determination of the eligibility of a patient for subsidy and the amount and form of subsidy are based on a uniform criteria, which are based on defined measures of patient financial need including annual income below a multiple of the federally defined poverty level, set by the clearinghouse across all foundations participating in the clearinghouse network, wherein the pharmaceutical providers contributions are not conditional on only their own brand of drug being prescribed to the patient or only their choice of a provider or specific pharmacy being used, wherein the requested drug may or may not be manufactured by the pharmaceutical providers participating in the network, wherein the burden of supporting brand of drugs manufactured by non-participating pharmaceutical providers is shared by the participating pharmaceutical providers in a manner proportional to the benefit derived by the pharmaceutical provider in the form of its own drug subsidies through the clearinghouse relative to the other pharmaceutical participants, wherein there is no data exchange between the clearinghouse and the pharmaceutical provider or between the foundations and pharmaceutical providers that allows pharmaceutical subsidy providers to correlate their donations to the number of prescriptions subsidized by a charity, and wherein the clearinghouse system is configured such that giving and receiving the subsidy is double-blind, so that the one or more pharmaceutical providers do not know which foundation requested and patient received the subsidy, and the foundation and patient do not know which one or more pharmaceutical providers provided the subsidy.

14. The system of claim 13, the at least one clearinghouse processor comprising:

an intake processor configured to determine if the foundation is in the network of foundations.

15. The system of claim 13, wherein the at least one clearinghouse processor is configured to determine if the drug is available from a pharmaceutical provider from the network of pharmaceutical providers and, if so, to request the subsidy from the pharmaceutical provider in the form of only the drug.

16. The system of claim 13, wherein the at least one clearinghouse processor is configured to determine if the drug is available from a pharmaceutical provider from the network of pharmaceutical providers and, if so, to request the subsidy from the pharmaceutical provider in the form of only the drug and cash.

17. The system of claim 13, wherein the at least one clearinghouse processor is configured to determine if the drug is available from a pharmaceutical provider from the network of pharmaceutical providers and, if so, to establish a fair market value of the drug by requesting the pharmaceutical provider to provide at least a portion of the subsidy in the form of cash to enable procurement of the drug on the open market with the cash.

18. The system of claim 13, wherein the at least one clearinghouse processor is configured to determine if the drug is available from a pharmaceutical provider from the network of pharmaceutical providers and, if not, to:

determine an amount needed to procure the drug; and determine a cash portion of the amount to be paid by one or more of the pharmaceutical providers in the network of pharmaceutical providers.

19. The system of claim 18, wherein the at least one clearinghouse processor is configured to determine a pro rata portion of the cash portion to be paid by each of the one or more pharmaceutical providers, as a function of the total amount of all subsidies provided by the network of pharmaceutical providers.

20. The system of claim 13, wherein if the clearinghouse system receives multiple requests for the same drug for the same patient, the clearinghouse system is configured to select only one of the multiple requests for receipt of the subsidy.

21. The system of claim 13, wherein the clearinghouse system is configured to establish a low-cost pharmaceutical provider threshold, and the set of subsidy modules is configured to determine the subsidies such that pharmaceutical providers that provide drugs that cost less than the low-cost threshold do not subsidize pharmaceutical providers having drugs that cost more than the low-cost threshold.

22. The system of claim 13, wherein the clearinghouse system is configured to establish a low-cost pharmaceutical provider threshold, and the set of subsidy modules is configured to determine the subsidies such that pharmaceutical providers that provide drugs that cost less than the low-cost threshold provide subsidies in a smaller proportion than pharmaceutical providers having drugs that cost more than the low-cost threshold.

23. The system of claim 13, wherein the clearinghouse system is configured to apply a uniform and auditable standard of patient need assessment to determine eligibility for and the amount of subsidy.

24. The system of claim 13, wherein the clearinghouse is configured to provide the subsidy in the form of one or more coupons that can be applied against the drug costs and patient co-pay for any drug in a given disease state.

* * * * *